United States Patent [19]

Stuhmer et al.

[11] Patent Number: 4,944,761
[45] Date of Patent: Jul. 31, 1990

[54] BLADE-LIKE STEM FOR A FEMORAL HEAD PROSTHESIS

[75] Inventors: Karl-Gerhart Stuhmer, Ravensburg, Fed. Rep. of Germany; Rudolf Koch, Berglingen, Switzerland

[73] Assignee: Sulzer Brothers Limited, Winterthur, Switzerland

[21] Appl. No.: 447,687

[22] Filed: Dec. 8, 1989

[30] Foreign Application Priority Data

Jan. 10, 1989 [CH] Switzerland .............................. 70/89

[51] Int. Cl.⁵ .................................................. A61F 2/36
[52] U.S. Cl. ........................................ 623/23; 623/18
[58] Field of Search ........................ 623/23, 22, 18, 16

[56] References Cited

U.S. PATENT DOCUMENTS

| 2,719,522 | 10/1955 | Hudack | 623/23 |
| 4,068,324 | 1/1978 | Townley et al. | 623/23 |
| 4,661,112 | 4/1987 | Muller | 623/22 |
| 4,695,283 | 9/1987 | Aldinger | 623/23 |
| 4,728,334 | 3/1988 | Spotorno | 623/23 |

FOREIGN PATENT DOCUMENTS

| 0093869 | 11/1983 | European Pat. Off. | 623/23 |
| 0135755 | 4/1985 | European Pat. Off. | 623/22 |
| 0169976 | 2/1986 | European Pat. Off. | 623/22 |
| 0222236 | 5/1987 | European Pat. Off. | 623/23 |
| 2627569 | 12/1977 | Fed. Rep. of Germany | 623/23 |
| 3609119 | 9/1987 | Fed. Rep. of Germany | 623/23 |
| 2549718 | 2/1985 | France | 623/22 |
| 2573648 | 5/1986 | France | 623/22 |
| 2602672 | 2/1988 | France | 623/23 |

Primary Examiner—Ronald L. Frinks
Attorney, Agent, or Firm—Kenyon & Kenyon

[57] ABSTRACT

The stem of the femoral head prothesis has a distal zone of cylindrical cross-section and a proximal zone of rectangular cross section which extends from the distal zone. The sides of the stem in the proximal zone are plane with outstanding parallel ribs which can be driven into the spongy tissue of a femur bone. The ribs on the anterior side of the stem are of a lower height than the ribs on the posterior side. The outermost ribs on each side provide for a resilient four-point bearing on the hard cortical shell of the fem>r bone. A pair of trochanter wings are provided on the narrow lateral side to penetrate into the cortical shell of the femur bone in order to preclude rotation of the stem within the bone.

12 Claims, 1 Drawing Sheet

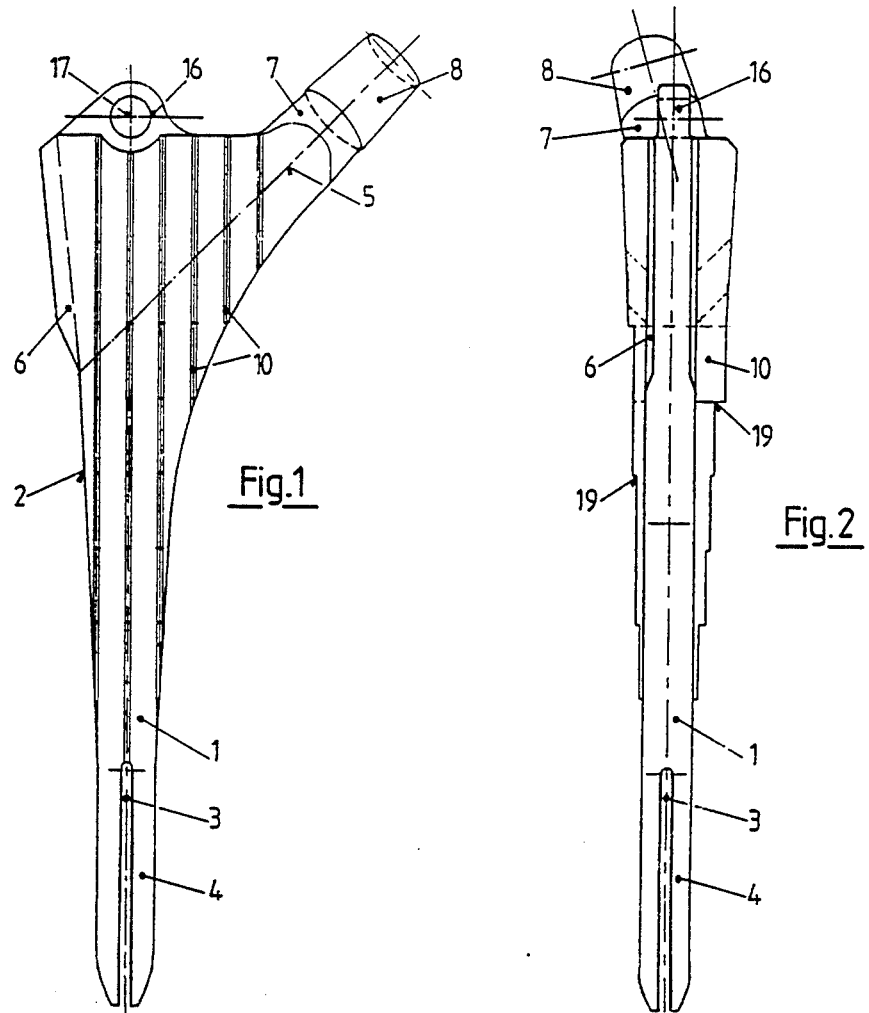
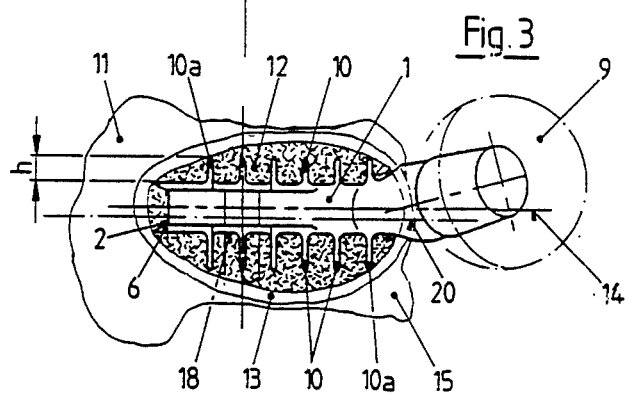

BLADE-LIKE STEM FOR A FEMORAL HEAD PROSTHESIS

This invention relates to a blade-like stem for a femoral head prosthesis and, more particularly, to a blade-like stem for a femoral head prosthesis.

Heretofore, various types of stems have been known for the implantation of a femoral head prosthesis in a femur. For example, prosthesis stems for a femur have been known which employ outstanding ribs on a proximal part of the stem in order to engage within a femur bone. Examples of such constructions are described in French Pat. No. 2,602,672; German OS No. 36 09 119 and European Patent Application No. 0 135 755.

Other prostheses stems have also been known which employ elongated ribs or grooves along the entire length of the stem or only within a proximal zone of the stem. Examples of such constructions are described in U.S. Pat. No. 2,719,522; European Patent Application No. 0 169 976 and French Pat. Nos. 2,549,718 and 2,573,648.

Still other prosthesis have been know which employ an arcuate stem formed of stepped construction. Examples of such are described in U.S. Pat. No. 4,068,324 and European Patent Application No. 0 093 869.

In particular, European Patent No. 0 222 236 describes a fixing stem having a blade-like stem in which a proximal zone is curved in the fashion of a kidney or banana in cross-section. In addition, the stem is provided with a plurality of sharp-edge ribs which extend in parallel to the longitudinal axis of the proximal part and which extend outwardly from opposite sides of the stem. In this respect, the ribs have been of different heights so that the outer envelope shape of the stem cross-section resembles a highly curved convex lens. The purpose of such a shape is to optimize adaptation of the stem to the anatomical conditions in the proximal zone of a femur bone. In this case, the substantially lens-like zone of the spongy tissue of the bone is "filled" by the lens shape of the stem. However, when a stem of the above type is implanted into a femur bone, there is a risk that the projecting ribs may break through the cortical shell of the bone.

Accordingly, it is an object of the invention to provide a resilient four-point bearing of a stem for a femoral head prosthesis on the hard cortical shell of a femur bone.

It is another object of the invention to be able to soften the transfer of loading forces from a prosthesis stems to a bone cortex.

It is another object of the invention to provide a stem for a femoral head prosthesis which is particularly adapted to the anatomical conditions in the proximal zone of a femur bone.

Briefly, the invention provides a blade-like stem for a femoral head prosthesis which has a distal zone and a proximal zones of rectangular cross-section which extends from the distal zone along a longitudinal axis and which widens in a medial direction and a lateral direction longitudinally thereof. In addition, the proximal zone has a plane posterior side and a plane anterior side from each of which a plurality of shape-edge ribs extend in parallel to the axis of the proximal zone for implanting in the spongy tissue of a femur. In addition, the ribs on the anterior side are of less height than the ribs on the posterior side. Also, the outermost ribs on each side are sized to bear on the hard cortical shell of the femur bone to define a resilient four point bearing on the cortical shell with the innermost ribs disposed within the spongy tissue and spaced from the cortical shell.

The cross-sectional shape of the stem is such as to take account of that for an anatomically correct "position" of a femoral head. Thus, the center plane of the stem which extends from the lateral zone to the medial zone is offset in the anterior direction relative to the corresponding plane of the bone.

In order to prevent "break out" of the cortical shell which narrows conically in the distal direction, the ribs on each side of the stem decrease in height in stepwise fashion in the distal direction.

The stem is also provided with a prosthesis neck which extends from the proximal zone. This neck is disposed on an axis in a plane forming an angle on the anterior side of the proximal zone with a longitudinal center plane of the proximal zone.

Still further, the stem is provided with a pair of trochanter wings each of which extends laterally from a respective side of a proximal zone and longitudinally from a point of intersection of the neck axis with a lateral narrow side of the proximal zone. Each wing is also provided with a sharp edge to embed in the cortical shell so as to provide an additional safeguard against accidental rotation of the stem.

These and other objects and advantages of the invention will become more apparent from the following detailed description taken in conjunction with the accompanying drawings wherein:

FIG. 1 illustrates a side view of a stem constructed in accordance with the invention;

FIG. 2 illustrates a view of the stem of FIG. 1 from the lateral side; and

FIG. 3 illustrates a plan view of the stem of 1 implanted in a femur bone and intended for the left-hand side of a body.

Referring to FIG. 1, the stem 1 for a femoral head prosthesis has a distal zone which is of cylindrical cross-section. As indicated, the cylindrical distal zone extends over approximately one-quarter to one-third of the height of the stem and has a surface which is polished smoothly to improve sliding. This distal zone is provided with a plurality of longitudinal slots 3 and a central axial bore extending on a longitudinal axis of the stem. A slotted wall 4 which remains, along with the bore, provides a mobility to the wall segments which enables the stem 1 to yield to unevenness in an evacuated narrow channel of a femur.

The stem 1 also has a proximal zone of rectangular cross-section which extends from the cylindrical distal zone along the longitudinal axis. As indicated, the proximal zone widens continuously in the medial direction and the lateral direction longitudinally of the axis of the stem. In the medial direction, the stem 1 extends on an arc which terminates in a prosthesis neck 7 which, in turn, carries a conical pin 8 for receiving a joint head 9 (see FIG. 3).

As shown in FIG. 1, the neck 7 extends from the proximal zone on an axis 5 which intersects with the narrow lateral side 2 of the stem 1 and which is also disposed in a plane which forms an angle on the anterior side of the proximal zone with a longitudinal center plane 14 of the proximal zone as indicated in FIG. 3. This angle is, for example from 5° to 15°. This ensures an optimum adaptation of the joint head position to the position of the natural femoral head which, because of the anterior and the spiral shape of the femoral bone, is also "turned" in the anterior direction.

Referring to FIGS. 1 and 2, a pair of trochanter wings 6 are disposed on the lateral side 2 of the proximal zone of the stem 1. As indicated in FIGS. 1 and 3, each wing extends laterally from a respective anterior and posterior side of the proximal zone of the stem 1. In addition, each wing 6 extends from a point of intersection of the neck axis 5 with the lateral narrow side 2 of the proximal zone of the stem in the proximal direction. In addition, each wing 6 has a sharp edge.

Referring to FIG. 3, each of the anterior and posterior sides 18 of the stem 1 is plane and is provided with sharp-edge ribs 10 which extend in parallel to the longitudinal axis of the stem 1. At least a majority of the ribs 10 on the posterior side are of a greater height than the ribs 10 on the anterior side with the ribs on the anterior side being of equal height h to each other. In this respect, the sides 18 of the stem 1 are parallel to each other and to the center plane 14. The anterior and posterior "directions" will be apparent from FIG. 3 with reference to the position of the lesser trochanter 15 which, of course, is directed slightly in the posterior direction. Also, the rib height h which is constant for all the ribs on one side 18 of the stem 1 decreases in stepwise manner 19 as indicated in FIG. 2 on both sides of the stem from the proximal region to the distal region in order to reduce the risk of the bone 11 "breaking out".

As indicated in FIG. 3, the plane sides 18 of the stem and the constant height of the ribs 10 have the effect that, besides the trochanter wings 6, only the outermost rib 10a on each side of the stem 1 bears on the hard cortical shell 13 of the femur bone so that a resilient four-point bearing of the stem 1 in the bone 11 is achieved. The innermost ribs 10 extend only into the spongy tissue 12 of the bone 11 which, as shown in cross-section, is substantially lenticular.

As indicated in FIG. 3, the resilient four point bearing of the stem on the hard cortical shell of the femur bone 11 provides for a soft transmission of forces from the prosthesis stem 1 to the bone.

Of note, different posterior and anterior rib heights h are shown so that the center plane 14 of the stem 1 is offset in the anterior direction from the center plane 20 of the bone for optimal positioning of the joint head 9.

Referring to FIGS. 1 and 2, the stem 1 is provided with a horizontal shoulder at the proximal end which extends from the wing 6 to the neck 7. In addition, a projection 16 extends from the horizontal shoulder and is formed with a bore 17 which is effective as a place to engage a withdrawing instrument in the event of a reoperation.

The invention thus provides a stem for a femoral head prosthesis which is more readily adapted to the lenticular shape of a femur bone and which provides for a soft transmission of forces between the prosthesis stem and the femur bone.

What is claimed is:

1. A blade-like stem for a femoral head prosthesis having
   a distal zone of cylindrical cross-section, said zone including a plurality of longitudinal slots;
   a proximal zone of rectangular cross-section extending from said distal zone along a longitudinal axis, said proximal zone widening continuously in a medial direction and a lateral direction longitudinally thereof and having two plane sides;
   a plurality of sharp-edged ribs extending from each said plane side of said proximal zone in parallel to said longitudinal axis, at least a majority of said ribs on a posterior one of said sides being of greater height than said ribs on an anterior one of said sides, said ribs on said anterior side being of equal height to each other; and
   a prosthesis neck extending from said proximal zone, said neck being disposed on an axis in a plane forming an angle on said anterior side of said proximal zone with a longitudinal center plane of said proximal zone.

2. A stem as set forth in claim 1 wherein each said rib decreases in height in stepwise manner in a distal direction.

3. A stem as set forth in claim 2 which further comprises a pair of trochanter wings, each said wing extending laterally from a respective one of said sides of said proximal zone and longitudinally from a point of intersection of said neck axis and a lateral narrow side of said proximal zone, each said wing having a sharp edge.

4. A stem as set forth in claim 1 which further comprises a pair of trochanter wings, each said wing extending laterally from a respective one of said sides of said proximal zone and longitudinally from a point of intersection of said neck axis and a lateral narrow side of said proximal zone, each said wing having a sharp edge.

5. A stem for a femoral head prosthesis having
   a distal zone;
   a proximal zone of rectangular cross-section extending from said distal zone along a longitudinal axis, said proximal zone widening in a medial direction and a lateral direction longitudinally thereof and having a plane posterior side and a plane anterior side; and
   a plurality of sharp-edged ribs extending from each said side in parallel to said axis for implanting in spongy tissue of a femur, said ribs on said anterior side being of less height than said ribs on said posterior side, the outermost ribs on each said side being sized to bear on a hard cortical shell of the femur bone to define a resilient four point bearing on the cortical shell with the innermost ribs disposed within the spongy tissue and spaced from the cortical shell.

6. A stem as set forth in claim 5 which further comprises a pair of trochanter wings, each wing extending laterally from a respective one of said sides of said proximal zone.

7. A stem as set forth in claim 5 further comprises a prosthesis neck extending from said proximal zone, said neck being disposed on an axis in a plane forming an angle on said anterior side of said proximal zone with a longitudinal center plane of said proximal zone.

8. A stem as set forth in claim 7 which further comprises a pair of trochanter wings, each said wing extending laterally from a respective one of said sides of said proximal zone an longitudinally from a point of intersection of said neck axis and a lateral, narrow side of said proximal zone, each said wing having a sharp edge.

9. A stem as set forth in claim 7 wherein said angle is from 5° to 15°.

10. A stem as set forth in claim 5 wherein each rib decreases in height in stepwise manner in a distal direction.

11. A stem as set forth in claim 5 wherein said distal zone is of cylindrical cross-section and has a plurality of longitudinal slots therein to impart resilience to said distal zone.

12. A stem as set forth in claim 5 wherein said sides are parallel to each other.

* * * * *

UNITED STATES PATENT AND TRADEMARK OFFICE
CERTIFICATE OF CORRECTION

PATENT NO.   :   4,944,761

DATED        :   July 31, 1990

INVENTOR(S) :   KARL-GERHART STUHMER, et al

It is certified that error appears in the above-identified patent and that said Letters Patent is hereby corrected as shown below:

On the title page:

In the Abstract, line 10 "fem>r" should be -femur-
Column 1, line 23 "know" should be -known-
Column 1, line 58 "zones" should be -zone-
Column 4, line 54 "zone an" should be -zone and- Signed and Sealed this Fourteenth Day of January, 1992

*Attest:*

HARRY F. MANBECK, JR.

*Attesting Officer*    *Commissioner of Patents and Trademarks*